United States Patent [19]

Averill

[11] 4,285,070

[45] Aug. 25, 1981

[54] PROSTHETIC DEVICE

[75] Inventor: Robert G. Averill, Ringwood, N.J.

[73] Assignee: Minnesota Mining and Manufacturing Company, St. Paul, Minn.

[21] Appl. No.: 160,612

[22] Filed: Jun. 18, 1980

Related U.S. Application Data

[63] Continuation of Ser. No. 912,075, Jun. 5, 1978, abandoned.

[51] Int. Cl.$^3$ .............................................. A61F 1/03
[52] U.S. Cl. .................................. 3/1.911; 128/92 C
[58] Field of Search ..................... 3/1.911, 1.91, 1.9; 128/92 C

[56] References Cited

U.S. PATENT DOCUMENTS

| | | | |
|---|---|---|---|
| 3,878,566 | 4/1975 | Bechtol | 3/1.91 |
| 3,924,277 | 12/1975 | Freeman et al. | 3/1.911 |
| 3,927,423 | 12/1975 | Swanson | 3/1.91 |
| 3,964,106 | 6/1976 | Hutter et al. | 3/1.911 |
| 4,007,495 | 2/1977 | Frazier | 3/1.91 |
| 4,016,606 | 4/1977 | Murray et al. | 3/1.911 |
| 4,041,550 | 8/1977 | Frazier | 3/1.91 |
| 4,094,017 | 6/1978 | Matthews et al. | 128/92 C X |
| 4,136,405 | 1/1979 | Pastrick et al. | 128/92 C X |
| 4,151,615 | 5/1979 | Hall | 3/1.91 |
| 4,158,894 | 6/1979 | Worrell | 3/1.91 |

Primary Examiner—Clifford D. Crowder
Attorney, Agent, or Firm—Cruzan Alexander; Donald M. Sell; Edward T. Okubo

[57] ABSTRACT

A patella prosthesis having a plurality of bearing surfaces designed to provide low-friction interaction throughout the entire range of leg extension and flexure with a metal condylar replacement prosthesis is disclosed. The prosthesis provides a combination of a reinforced patella surface and a femoral prosthetic surface having both a prolonged anterior flange and a central opening for the passage of the cruciate ligaments.

4 Claims, 16 Drawing Figures

PROSTHETIC DEVICE

This is a continuation of application Ser. No. 912,075 filed June 5, 1978, now abandoned.

BACKGROUND OF THE INVENTION

The present invention relates to a patella prosthesis and particularly to the patellar prosthetic surface designed to articulate with the femoral component of a total knee prosthesis. The patellar bearing surface is preferably made of a physiologically inert polymer such as high density polyethylene supported by a physiologically inert metal such as a cobalt-chromium alloy. The patella prosthesis has a plurality of bearing surfaces designed to provide low friction interaction with a metal condylar replacement prosthesis throughout the entire range of leg extension and flexure. The femoral component includes not only a prolonged anterior flange for extended articulation with the patella throughout the excursion of the latter but also includes a medial slot for retention of the cruciate ligaments.

Knee prosthetic devices are now available in many gradations of intrinsic stability depending upon the degree of damage to the knee. The surgeon's goal should be to replace only those functions of the joint which need replacement, preserving as much of the body structure as possible, minimizing the demands placed upon the prosthetic device and preserving as much bone as possible so that the remaining bone can act as foundation for further repair or replacement. The surgical procedure should provide relief from disabling pain, restore functional motion with maximal potential for lasting results and should include adequate provision for satisfactory salvage in the event of failure.

The most common cause of knee trauma or dysfunction is impairment of the frictional interface between the femoral condyles and the cooperating tibial plateau. Such damage is usually brought on by arthritic disease. Where the ligamentous structures of the knee are reasonable intact, a less intrinsically stable resurfacing type prosthesis is indicated than the bulky, complicated so-called "hinge" type prosthesis previously used. The resurfacing type prostheses are well known and are described with slight variations in U.S. Pat Nos. 3,715,763, 3,728,742, 3,774,244 and others. These partial knee replacements usually consist of a combination of a metal component replacing one or both condylar surfaces of the femur and a polymeric replacement for the tibial plateau which may have varying degrees of congruence with the complementing femoral component. The combination is intended to provide a sliding and/or rolling action in cooperation with the existing knee capsule and ligaments thereby providing a functional knee. These mono-condylar or dual-condylar replacements may or may not provide central clearance for the cruciate ligaments which are considered to be important to knee stability and function.

A more intrinsically stable prosthesis is suggested when the capsule and colateral ligaments are intact but the cruciate ligaments are damaged. In this case there is no need to provide for retention of the cruciate ligaments and the means for attaching the prosthesis to the bone can be more substantial, particularly the tibial component which can now incorporate a center spike or shaft for better securement.

When there is poor ligamentous stability, a prosthesis with complete intrinsic stability is more applicable, that is, a device which provides a mechanical linkage between the femoral and tibial components. Many of the presently favored "linked" knee devices use a combination of bearing geometrics and mechanical tee bars in contrast to the more constrained earlier "hinge" devices which offered only one degree of freedom.

It is difficult to place the many knee prosthetic devices into exact categories since there are many variations and combinations in use. In view of the relative newness of these devices, which have been in general use for only a few years, there is still controversy over optimum design. One school of thought holds that devices should approximate the shapes of the natural bone which they replace so that the resultant prosthetic action will more closely approximate the functions and actions of the natural joints. Others reason that since the properties of prosthetic materials are different than those of the natural bones and since material processing and finishing techniques have reproducibility limits, the design must compromise normal anatomical design to achieve lasting functional results within the limitations imposed by the available materials.

Although the resurfacing type prosthesis has only been in general use for the past five years or so, it has been widely accepted. One problem that has been encountered in some cases has been anterior knee pain, patellar in origin, after knee replacement. In some cases, the range of movement post-operatively has been limited to less than 90° because of this patellar pain. The patella serves as a fulcrum for the tendons and ligaments which straighten the leg and disruption of articulation of the patella following knee replacement can increase the quadriceps force required for full extension of the leg by 15 to 30 percent. Pain appears to be aggravated during extension stress such as walking up and down stairs and is concentrated around the patella.

In an effort to alleviate this problem, many of the more recent femoral dual-condylar elements have been designed to provide for prolongation of the anterior flange so that the metal groove articulates with the patella throughout the excursion of the latter. Unfortunately, to provide articulation of the patella and femoral prosthesis throughout the entire range, it was usually necessary to omit the central opening through which the cruciate ligaments pass. Thus, the surgeon was faced with a choice—the important cruciate ligaments could be retained or full patellar articulation could be provided.

The cruciate ligaments stabilize the knee in the anterior-posterior (front-to-back) direction while allowing the joint to flex freely. The two side-by-side ligaments are in the form of an X, one fastened to the anterior of the femur and the posterior of the tibia while the other is fastened posterior to the femur and anterior of the tibia.

The patella is a sesamoid bone imbedded in the extensor tensor of the knee. The primary function of the patella is to increase the efficiency of the quadriceps muscles. The quadriceps femoris is a powerful combination of four muscles which extend or straighten the leg. The patella also serves as a connection between the quadriceps tendon and the patellar ligament. The patella has a ridge on its posterior which slides in the groove between the femoral condyles. The patella in combination with the patellar track and mating portions of the femoral condyles acts as a low friction pulley mechanism for the quadriceps tendon so that the extension force can be carried with efficiency and stability around the curvature of the flexed knee. Unless the patella can slide freely around the knee during flexion and extension, it can cause pain and/or weakness.

Unfortunately, the combination of synthetic or artificial surfaces in contact with natural body materials does not provide a long-term low-friction combination. The patella is meant to function against natural joint surfaces and tends to be unreliable when caused to articulate against metallic surfaces. This problem was solved by a polymeric insert or facing applied to the posterior of a resected patella, which insert would then slide with low friction over the surface of the metal femoral implant.

The problem restated is that known patella prosthetic devices which provide adequate bearing contact with femoral implants through prolonged anterior flanges make no provision for passage of the cruciate ligaments through the femoral component. Femoral implants having a passage for the cruciate ligaments currently offer inadequate bearing contact with the natural patella or with synthetic patella prosthetic surfaces.

SUMMARY OF THE INVENTION

The present invention provides a combination of a reinforced prosthetic patellar surface and a femoral prosthetic surface having both a prolonged anterior flange and a central opening for the passage of the cruciate ligaments. Both the prosthetic patellar surface and the femoral prosthetic surface are designed so that the surfaces articulate freely and accurately throughout the normal limits of knee flexion and extension. This is accomplished by having a central ridged area of the polymeric prosthetic patellar surface which articulates freely within a central groove of the prolongated anterior flange of the metal femoral component and also by having two concave bearing surfaces at its outer edge which slide over the parallel condylar surfaces of the femoral component adjacent to the opening for the cruciate ligaments. The patella prosthesis would normally be made of a physiologically inert polymer, preferably ultra high density polyethylene, and would be backed by a thin reinforcing layer of metal, preferably cobalt-chromium alloy.

BRIEF DESCRIPTION OF THE DRAWINGS

The invention will be better understood by reference to the following description of an exemplary embodiment taken in conjunction with the figures of the accompanying drawings, in which:

FIG. 2 is a side view and FIG. 3 is an end view thereof;

FIG. 4 is a view of the posterior of the assembly; FIG. 5 is a side view; FIG. 6 is an end view and FIG. 7 is a sectional view taken along the line 7—7 of FIG. 4;

DETAILED DESCRIPTION OF THE INVENTION

Figure 1:
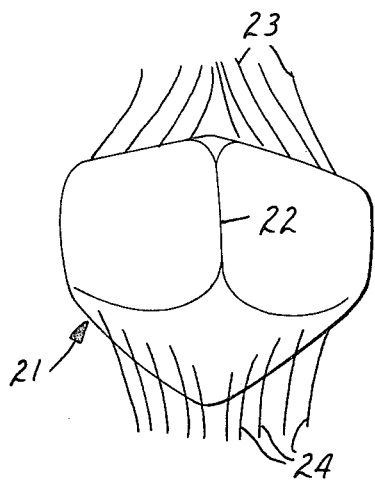
FIGS. 1, 2 and 3 are three views of a natural patella, FIG. 1 being a top view of the posterior of the patella.
Figure 2:
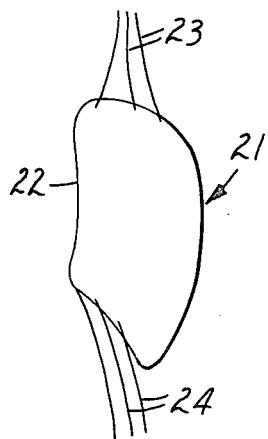
Figure 3:
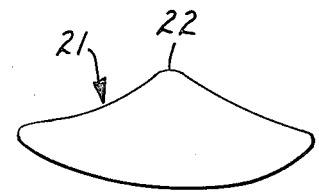
Figure 4:
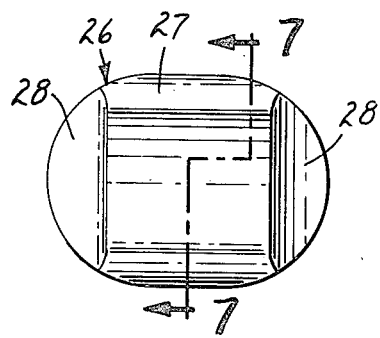
FIGS. 4, 5, 6 and 7 show assemblies of the patellar implant of the present invention assembled to a resected natural patella.

Referring more particularly to the drawings, FIGS. 1 to 3 show three views of a natural patella 21. As can be seen especially in FIGS. 1 and 3, the patella has a very pronounced ridge 22, which slides along the patellar surface of the femur and the intercondylar notch during extension or flexion of the knee. Attached to the upper surface of the patella, is the quadriceps tendon 23, leading to the quadriceps muscles which provide power for extension of the knee. Attached to the lower surface of the patella is the patellar ligament 24 which connects the patella to the tibia. FIG. 2 shows a side view and FIG. 3 shows an end view of the patella.

The patellar prosthetic surface of prior art patellar prosthetic devices are usually made of plastic, e.g., "Teflon" or ultra high molecular weight polyethylene. The devices may be adhesively secured to the resected natural patella or they may be mechanically interlocked or combinations of both adhesive and mechanical fastening may be used. In all cases, the prior art devices had a generally disc or dome shaped surface which was intended to slide in a matching rounded groove of the femoral prosthetic component. If such a patellar prosthetic surface were to be used in combination with a femoral prosthesis having a central opening for retention of the cruciate ligaments, the possibility existed for the patella implant to drop into the cruciate opening during extreme flexure of the knee.

FIGS. 4, 5, 6 and 7 show assemblies of the patella implant of the present invention assembled to the resected natural patella. The contact or bearing surface 26 of the patella implant would normally be made of a durable, physiologically acceptable polymer such as ultra-high molecular weight polyethylene which would provide low sliding friction against the metal femoral prosthesis 35. Although the shape of the surface could vary within sound engineering limits and based upon the design of the complementary femoral prosthesis, the surface would include both a central so called ridge portion 27, intended to track within the groove 38 of the extended anterior flange of the femoral prosthesis, and shoulders 28, which are intended to slide upon the prosthetic condylar surfaces 37 particularly over that portion of the femoral prosthesis where there is space 36 between the condylar surfaces for passage of the cruciate ligaments. Again, the shoulders 28 may take any shape commensurate with sound engineering practices provided that they are complementary to the femoral prosthesis design and providing that they make sliding contact with at least one prosthetic condylar surface 37 and preferably two such prosthetic surfaces. The size and shape of the patellar prosthetic surface is immaterial although the devices will generally be available in several standard sizes which generally match the size and shape of the natural patella.

Figure 5:
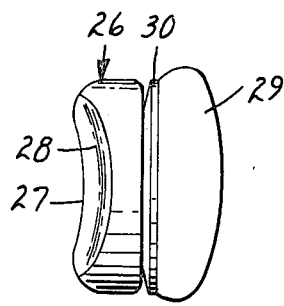
Figure 6:
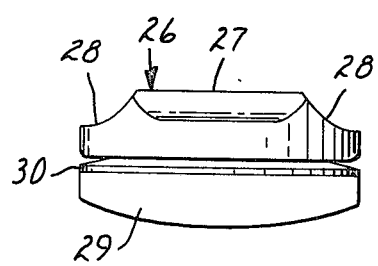

In the side view shown in FIG. 5, both the central ridge portion 27 and the shoulder portions 28 have a surface curvature that matches the respective mating surfaces of the complementary femoral prosthesis. Exact matching of the complementary surfaces may not be necessary from a friction standpoint and may not always be possible because of compound curvatures found on many femoral prosthesis designs. However, it is preferable to match the curvatures as closely as possible to reduce wobble and to reduce wear.

With the aid of an oscillating saw or similar purpose surgical tool, the articular surface and a slice of 3–4 mm. in thickness of subchondral bone is tangentially resected from the natural patella 21, carefully preserving the ventral part 29. Thus, the continuity of the quadriceps tendon into the patellar ligament is not interrupted. Attached to the ventral part 29 of the patella 21, is the patella base 30, and to this is attached the bearing insert 26, previously discussed. The patella base 30 is preferably made of physiologically acceptable metal such as cobalt-chrome alloy or stainless steel. The patella base 30 is an integral part of the invention in that it provides support or reinforcing for both the bearing insert 26 and the resected patella 21. The natural patella and such patella implants as are known to the art are lacking in tensile stiffness since they are intended for compressive stress under usage. The present invention would be subject to considerable tensile stress when supported only by the outer shoulders while bridging over the cruciate ligament opening.

Figure 7:
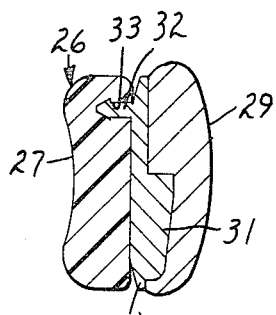
Figure 8:
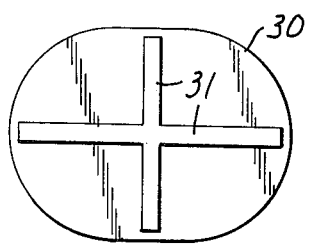
FIGS. 8 and 9 are two further views of the patellar implant of the present invention.
Figure 9:
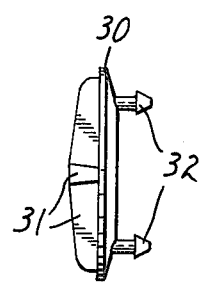

In the preferred form of the patella base 30 shown in FIGS. 7 to 9, the patella base has intersecting ridges 31 which fit into slots cut into the resected patella, the inlaid ridges serving to position the base, provide retention, and provide some degree of lateral reinforcement. On its reverse, the base 30 contains 4 barbed pins 32 which lock into matching holes 33 in the back of the bearing insert 26. Such locating and fastening protrusions are not considered essential to the invention. Other means of mechanical fastening, adhesive fastening or combinations of these may alternatively be used.

Figure 10:
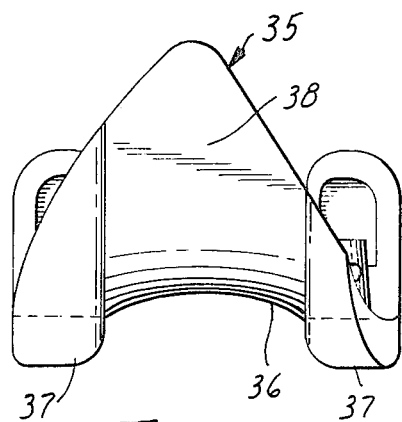
FIGS. 10, 11 and 12 are, respectively, front, side and bottom views of the femoral prosthesis of the present invention.
Figure 11:
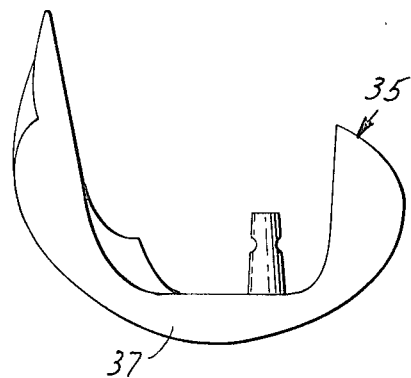
Figure 12:
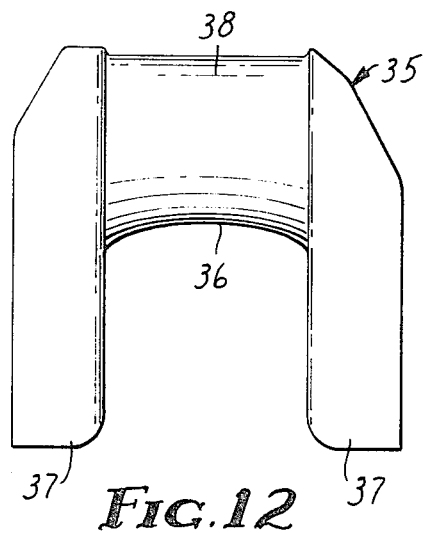

FIGS. 10, 11 and 12 show the preferred design of the femoral prosthesis 35 to be used with the patella prosthesis of the present invention. The design is preferentially furnished in the form of separate models for left and right knee usage.

Figure 13:
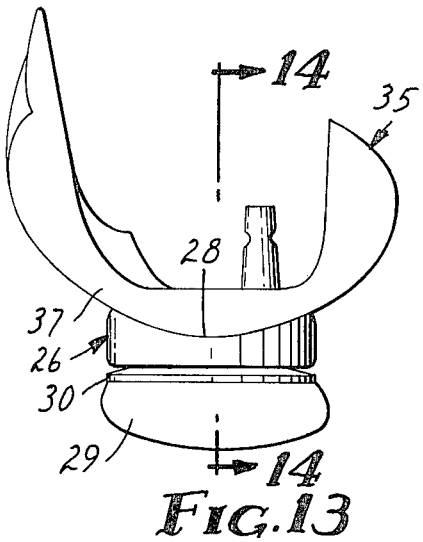
FIG. 13 is a view showing the relative positions of the patella prosthesis and the femoral prosthesis during full flexion of the knee joint.
Figure 14:
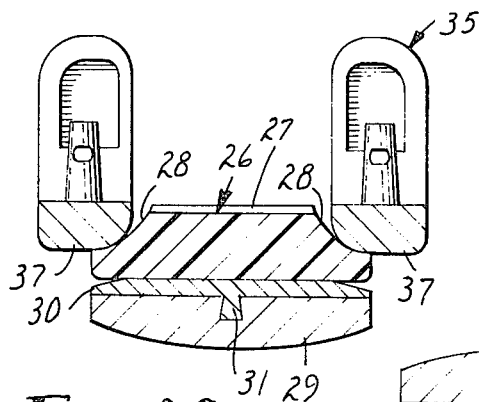
FIG. 14 is a sectional view taken along the line 14—14 of FIG. 13.

FIGS. 13 and 14 show the relative positions of the patella prosthesis and the femoral prosthesis during full flexion of the knee joint. At this position, the patella is stradling the cruciate ligament opening 36 of the femoral prosthesis and is supported only by the condylar surfaces 37.

Medial/lateral stability of currently used patella prostheses is another problem which this design overcomes due to the side bearings which contain the patella throughout the flexion range. The problem would probably be most acute when extension is started from full flexion, as when the patient starts to arise from a chair. The knee joint would be in the position shown in FIGS. 13 and 14. As these figures show, the design of the present invention provides excellent medial/lateral stability.

Figure 15:
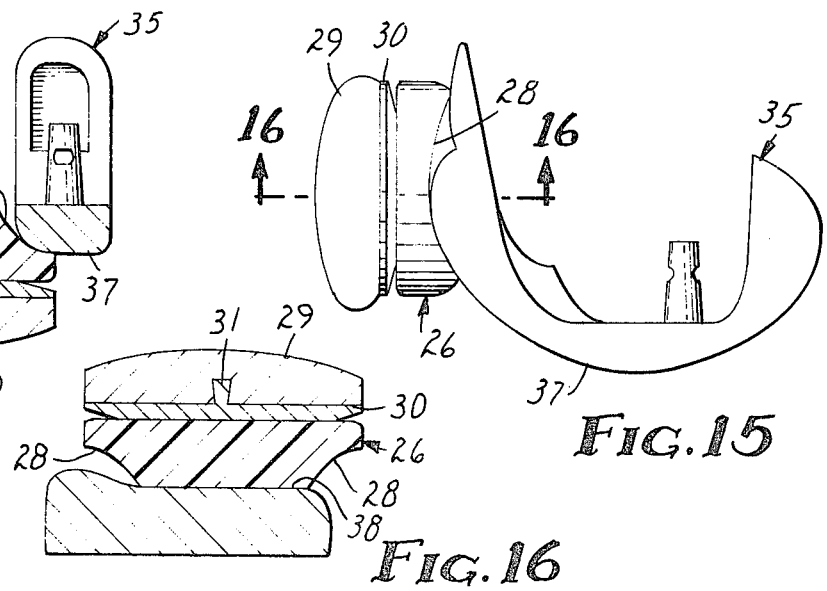
FIG. 15 is another view showing the relative positions of the patella prosthesis and the femoral prosthesis during full extension of the knee joint.
Figure 16:
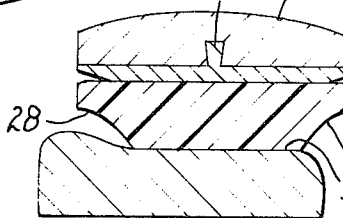
FIG. 16 is a sectional view taken along the line 16—16 of FIG. 15.

FIGS. 15 and 16 show the relative positions of the patella prosthesis and the femoral prosthesis during full extension of the knee joint. It can be seen that in this position the contact area is primarily between the central ridge 27 of the patellar surface and the central groove 38 of the femoral prosthesis. While the outer shoulders 28 of the patellar surface are not needed for bearing contact as the joint approaches full extension, they continue to provide for medial/lateral stability. The restraining effect of the shoulders 28 is not very evident in FIG. 16 but may be clearly seen in FIG. 15.

What is claimed is:

1. A knee joint prosthesis comprising a patella prosthesis for sequential articulation against the condylar surfaces and the surface of the central medially-laterally flat and longitudinally convex groove in an anterior flange bridging said condylar surfaces of a femoral prosthesis having a central opening therein for passage of the cruciate ligaments, said patella prosthesis comprising a substantially flat base, having an outline comprised of two parallel sides and semicircular end portions, one surface of which is adapted for attachment to the resected surface of the natural patella, a bearing insert having a peripheral outline substantially coextensive with said base and having a central laterally extending medially-laterally flat and longitudinally concave ridge portion adapted for sequential tracking within the medially-laterally flat and longitudinally convex groove in the anterior flange of said femoral prosthesis and a pair of shoulders having a shape complementary to the condylar surfaces of said femoral prosthesis for sliding contact with said surfaces during flexion of the knee joint, said central laterally extending medially-laterally flat and longitudinally concave ridge portion and said pair of shoulders thus providing medial and lateral stability to the patellar prosthesis.

2. A knee joint prosthesis according to claim 1 wherein the surface of the base of the patellar prosthesis for attachment to the resected natural patella is provided with intersecting ridges adapted to be received into corresponding slots cut into the resected patella, said ridges thereby orienting said base on said resected patella and providing stability between said patella and patellar prosthesis.

3. A knee joint prosthesis according to claim 2 wherein the other surface of said base includes a plurality of projections extending from said surface and adapted to be inserted into corresponding apertures provided in said bearing insert to secure said insert onto said base.

4. A knee joint prosthesis according to claim 1 wherein the central laterally extending medially-laterally flat and longitudinally concave ridge portion of said bearing insert is dissected at the ends thereof to form two transverse concave bearing surfaces comprising said pair of shoulders adapted for sliding contact with the condylar surfaces of said femoral prosthesis.

* * * * *